United States Patent

Bahrmann et al.

Patent Number: 6,020,532
Date of Patent: Feb. 1, 2000

[54] PROCESS FOR THE PREPARATION OF ALDEHYDES EMPLOYING CATALYST COMPOSITIONS BASED ON RHODIUM COMPLEXES CONTAINING DIPHOSPHINE LIGANDS

[75] Inventors: Helmut Bahrmann, Hamminkeln, Germany; Peter Lappe, Plano, Tex.; Thomas Müller, Dinslaken, Germany

[73] Assignee: Hoechst Aktiengesellschaft, Germany

[21] Appl. No.: 09/112,099

[22] Filed: Jul. 9, 1998

Related U.S. Application Data

[62] Division of application No. 08/839,330, Apr. 17, 1997, Pat. No. 5,992,634.

[30] Foreign Application Priority Data

May 15, 1996 [DE] Germany ............................ 196 19 527

[51] Int. Cl.⁷ .................................................. C07C 45/50
[52] U.S. Cl. ............................ 568/454; 568/451; 502/166
[58] Field of Search .................................. 568/454, 451; 502/166, 167, 168, 170, 213

[56] References Cited

U.S. PATENT DOCUMENTS

| | | | |
|---|---|---|---|
| 5,174,899 | 12/1992 | Bahrmann et al. | 210/644 |
| 5,347,045 | 9/1994 | Hermann et al. | 562/35 |

*Primary Examiner*—Gary Geist
*Assistant Examiner*—Sreeni Padmanabhan
*Attorney, Agent, or Firm*—Bierman, Muserlian and Lucas

[57] ABSTRACT

A process for preparing aldehydes by hydroformylating olefinically unsaturated compounds in the presence of a water-insoluble catalyst composition comprising rhodium complexes containing diphosphine ligands, wherein the diphosphine ligands present are compounds of the formula (I)

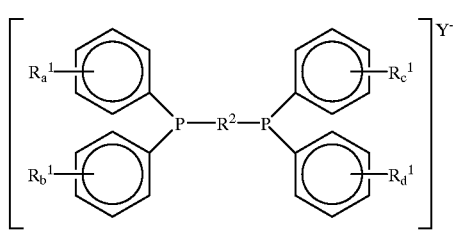

-continued

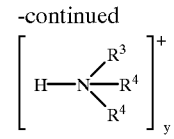

wherein $R^1$ is selected from the group consisting of carboxylate ($COO^-$), sulfonate ($SO_3^-$), phosphonate ($PO_3^{2-}$) and 2-anmino ethtanebisphosphonate, $R^2$ is selected from the group consisting of a straight-chain alkylene of 1 to 8 carbon atoms, an oxygen-containing alkylene of 2 to 6 carbon atoms, cycloalkylene of 3 to 10 carbon atoms and a member of the Formulae II, III, IV or v

II

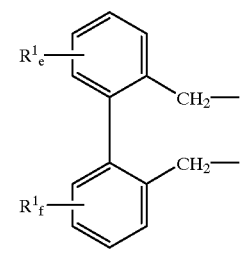

III

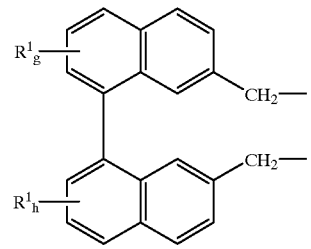

IV

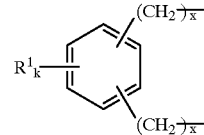

V

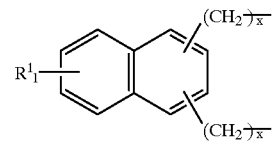

$a, b, c, d, e, f, g, h, k$ and $l$ are individually 0 to 1, where at least one of $a, b, c, d, e, f, g, h, k$ or $l$ has be equal to 1, $x(s)$ are individually 0 or 1, $y$ is an integer of 1 to 24, $R^3$ and $R^4$ are individually selected from the group consisting of alkyl of 4 to 26 carbon atoms, substituted or unsubstituted aryl of 6 to 10 carbon atoms, cycloalkyl of 6 to 10 carbon atoms and benzyl and $R^3$ can also be hydrogen and the use thereof in hydroformylations.

10 Claims, No Drawings

PROCESS FOR THE PREPARATION OF ALDEHYDES EMPLOYING CATALYST COMPOSITIONS BASED ON RHODIUM COMPLEXES CONTAINING DIPHOSPHINE LIGANDS

This Application is a Division of U.S. application Ser. No. 08/839330 filed Apr. 17, 1997 now U.S. Pat. No. 5,992,634.

FIELD OF THE INVENTION

The invention relates to new catalyst compositions based on rhodium complexes containing diphosphine ligands and their use in the preparation of aldehydes by reacting olefinically unsaturated compounds with hydrogen and carbon monoxide in a homogeneous phase.

STATE OF THE ART

Phosphines are used in a wide variety of industrial processes. Of particular importance is their use as ligands for metal complex catalysts, preferably containing as the central atom, a metal of group VIII of the Periodic Table of the Elements plus, if desired, in addition to the phosphine ligands, further groups capable of complex formation, The hydroformylation of olefins, which is widely carried out in industry, is increasingly carried out in the presence of catalyst systems based on rhodium complexes containing tertiary phosphines or phosphites as ligands. Since these ligands are generally present in excess, the catalyst composition comprises the complex and additional pure ligand. As these catalyst systems are soluble in organic media, the hydroformylation is carried out in a homogeneous phase. To separate off the reaction products and recover the catalysts homogeneously dissolved in the reaction product, the reaction product is generally distilled from the reaction mixture. However, due to the heat-sensitivity of the aldehydes formed, this is only possible for the hydroformylation of lower olefins having up to about 8 carbon atoms in the molecule.

The hydroformylation of long-chain olefins or olefinic compounds having functional groups results in the formation of high-boiling products which can no longer be satisfactorily separated from the catalyst by distillation. The thermal stressing of the material being distilled leads, as a result of thick oil formation, to considerable losses of desired product and to losses of catalyst as a result of decomposition of the complexes. This decisively reduces the economic attractiveness of the process.

It is known from EP-A-0 374 615 that organometallic complexes containing phosphorus(III) compounds as ligands can be separated off and recovered intact, i.e. without degradation of the catalytically active metal compound, from organic solvents using selective semipermeable polyaramid separating membranes. The driving force for the separation process can here be either a pressure difference (pressure filtration) or a concentration difference (dialysis). The process is particularly suitable for separating organometallic complexes and/or metal carbonyls containing phosphorus(III) compounds as ligands from organic solutions in which they have previously been employed as homogeneous catalysts.

Rhodium complexes mentioned in EP-A-0 374 615 are $HRhCO[P(C_6H_5)_3]_3$ and compounds which contain as ligands alkylammonium or arylammonium salts of sulfonated or carboxylated triarylphosphines of the formula

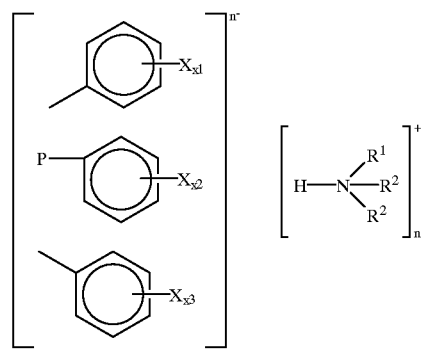

where X is a sulfonate ($SO_3{}_-$) or carboxylate ($COO^-$), $x^1$, $x^2$ and $x^3$ are 0 or 1, $R^1$ and $R^2$ are individually alkyl of 4 to 12 carbon atoms, aryl of 6 to 12 carbon atoms or cycloalkyl of 6 to 12 carbon atoms and $R^1$ can also be hydrogen.

Such rhodium complexes containing alkylammonium or arylammonium salts of sulfonated or carboxylated triarylphosphines as ligands are used for the hydroformylation of olefinically unsaturated compounds in a homogeneous phase but need to be stabilized by a large excess of free, uncomplexed ligands.

This high ligand excess leads in turn to a high salt concentration in the hydroformylation mixture and this high salt concentration can have an unfavorable influence on the reaction of the olefin with carbon monoxide and hydrogen since it impairs the solubility of the reactants in the reaction mixture and, in addition, promotes foaming. In the case of a membrane filtration which can be carried out after the hydroformylation to separate the catalyst system from the reaction product, the high ligand excess, i.e. the high salt concentration, also has an adverse effect. On the one hand, it reduces the transmembrane flux of the membrane filtration which can only be made up for by the use of very much larger membrane areas and on the other hand, it reduces the maximum degree to which the retentate can be concentrated. This leads, in the case of a recirculation of the catalyst-containing retentate to the hydroformylation reaction, to a reduction in the reactor volume available to the other reactants, an effect which, like the high membrane areas, lead to increased process costs and thus, reduces the economic attractiveness of the process.

The high salt concentrations also interfere in the case of a work-up of the hydroformylation mixture by distillation since they lead to an increased proportion of salt-containing thick oil.

OBJECTS OF THE INVENTION

It is an object of the invention to provide new catalyst compositions based on rhodium complexes containing organophosphorus ligands, which catalyst compositions can be used in the hydroformylation of olefinically unsaturated compounds in a homogeneous phase, lead to high activity and selectivity values in such a process and can be separated from the reaction mixture of the hydroformylation in a simple manner.

These and other objects and advantages of the invention will become obvious from the following detailed description.

THE INVENTION

The novel catalyst compositions of the invention are based on rhodium complexes containing diphosphine ligands, wherein the diphosphine ligands present are compounds of the formula

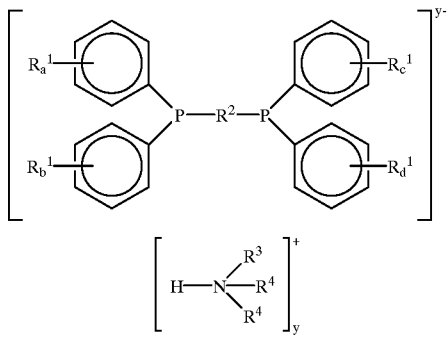

where $R^1$ is selected from the group consisting of carboxylate (COO$^-$), sulfonate (SO$_3^-$), phosphonate (PO$_3^{2-}$) and 2-aminoethanebisphosphonate [—NH—CH$_2$—CH(PO$_3^{2-}$)$_2$], $R^2$ is selected from the group consisting of a straight-chain alkylene of 1 to 8 carbon atoms, an oxygen-containing alkylene of 2 to 6 carbon atoms, cycloalkylene of 3 to 10 carbon atoms and a member of the formulae II, III, IV or V

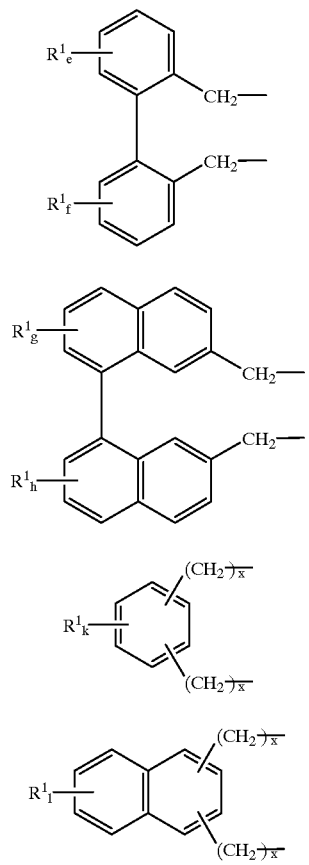

a, b, c, d, e, f, g, h, k, and l are individually 0 or 1, where at least one of a, b, c, d, e, f, g, h, k or l has to be equal to 1, x(s) are individually 0 or 1, $R^3$ and $R^4$ are individually selected from the group consisting of alkyl of 4 to 26 carbon atoms, substituted or unsubstituted aryl of 6 to 10 carbon atoms, cycloalkyl of 6 to 10 carbon atoms and, y is an integer of 1 to 24 benzyl and $R^3$ can also be hydrogen.

The compounds of formula I are in the form of ammonium carboxylates, sulfonates or phosphonates having a singly or multiply charged diphosphine anion and the corresponding number of ammonium cations as counter ions. They are generally insoluble or only sparingly soluble in water. In contrast, they have a good to very good solubility in organic solvents and are therefore particularly suitable for use in the organic phase.

Due to the incorporation of two trivalent phosphorus atoms, the compounds of formula I are very useful as chelating ligands in the catalyst compositions of the invention.

In formula I, $R^1$ is carboxylate, sulfonate, phosphonate or 2-aminoethanebisphosphonate, preferably sulfonate.

$R^2$ is a straight-chain alkylene of 1 to 8, preferably 1 to 5 carbon atoms and more preferably 1 to 3 carbon atoms. $R^2$ can also be an oxygen-containing alkylene of 2 to 6, preferably 2 to 4, carbon atoms and more preferably 4 carbon atoms as represented by —(CH$_2$)$_2$—O—(CH$_2$)$_2$—. $R^2$ can also be cycloalkylene of 3 to 10, preferably 6 to 10 carbon atoms or a member of formulae II, III, IV or V, preferably formula II.

In formulae I, II, III, IV and V, a, b, c, d, e, f, g, h, k and l are individually 0 or 1, where at least one of a, b, c, d, e, f, g, h, k or l has to be equal to 1. In compounds of formula I in which $R^2$ is a member of formula II, the sum of a, b, c, d, e and f, which indicates the number of $R^1$, is preferably 1 to 3. If $R^2$ is a member of formula III, the sum of a, b, c, d, g and h is preferably 1 or 2. If $R^2$ is a member of formula IV or V, the sum of a, b, c, d and k or a, b, c, d and l is preferably 1 to 3. If $R^2$ is a straight-chain alkylene of 1 to 8 carbon atoms, an oxygen-containing alkylene of 2 to 6 carbon atoms or cycloalkylene of 3 to 10 carbon atoms, the sum of a, b, c, and d is preferably 2 to 4.

In formula I, $R^3$ and $R^4$ are individually alkyl of 4 to 26, preferably 18 to 22 carbon atoms, substituted or unsubstituted aryl of 6 to 10 carbon atoms, preferably phenyl, cycloalkyl of 6 to 10 carbon atoms, preferably cyclohexyl, or benzyl. $R^3$ can also be hydrogen. Thus, the ammonium cations [H—NR$^3$R$^4$R$^4$]$^+$ are derived from secondary or tertiary amines NR$^3$R$^4$R$^4$ which contain a total of 8 to 78, preferably 12 to 72, more preferably 21 to 60, and most preferably 36 to 54, carbon atoms in $R^3$ and $R^4$. The ammonium cations are preferably derived from di-2-ethylhexylamine, tri-n-octylamine, triisooctylamine, triisononylamine, triisodecylamine, distearylamine, methyldistearylamine, triacetylamine or trieicosylamine.

As particularly suitable diphosphine anions in formula I are sulfonated diphosphine anions such as bis(disulfonatophenylphosphino) methane, 1,2-bis(disulfonatophenylphosphino)ethane, 1,3-bis(disulfonatophenylphosphino)propane, 1,4-bis(disulfonatophenylphosphino)butane, 1,5-bis(disulfonatophenylphosphino)pentane, bis(diphenylphosphinomethyl)ether and bis(diphenylphosphinoethyl) ether.

The compounds of formula I in which $R^1$ is sulfonate can be prepared by reacting a secondary phosphine oxide of the formula

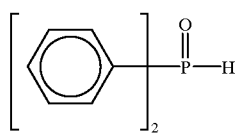

VI in the presence of a base with a dihalide of the formula $$X—R^2—X \qquad \text{VII}$$

where $R^2$ is as defined above and X is halogen, preferably chlorine or bromine, in the presence or absence of a solvent at −20 to 100° C. to obtain a diphosphine oxide of the formula

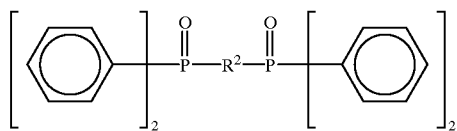

VIII reducing the diphosphine oxide of formula VIII in the presence or absence of a solvent with a silane of the formula $HSiCl_mR^5{}_n$, where m is 2 or 3, n is 0 or 1, m+n is equal to 3 and $R^5$ is methyl or phenyl at 80 to 160° C. to obtain a diphosphine of the formula

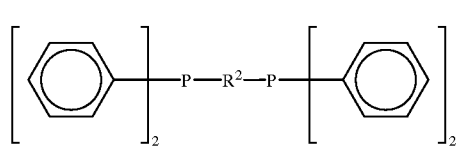

IX and sulfonating this diphosphine of formula IX at 0 to 50° C. using oleum, diluting the sulfonation mixture with water and adding the water-insoluble amine $NR^3R^4R^4$, from which the ammonium cation $[H—NR^3R^4R^4]^+$ in formula I is derived, dissolved in a water-insoluble organic solvent.

This synthesis process is described in detail in a U.S. patent application Ser. No. 839329 filed on the same day as the present application.

The invention further provides a process for preparing aldehydes by reacting olefinically unsaturated compounds with carbon monoxide and hydrogen in the presence of the above-described catalyst composition based on rhodium complexes containing diphosphine ligands of formula I.

The formation of the catalyst composition of the invention from rhodium or a rhodium compound and the diphosphine compound of formula I is carried out either in a step upstream of the hydroformylation, known as preformylation, or else, particularly in a continuous procedure, in situ during the hydroformylation reaction. The preformation upstream of the hydroformylation is preferably carried out in the same reactor in which the hydroformylation also takes place subsequently, but it can also be carried out in a separate reaction vessel.

To prepare the catalyst composition by preformation, the rhodium component (rhodium or a rhodium compound) is combined with the diphosphine compound of formula I, either in the hydroformylation reactor or in a separate apparatus. Here, both the rhodium or the rhodium compound and also the diphosphine compound of formula I are used in solution or, in the case of elemental rhodium, in suspension in an organic solvent. Suitable solvents are organic solvents which are inert under the conditions of the subsequent hydroformylation, for example toluene, ortho-xylene, meta-xylene, para-xylene, mixtures of isomeric xylenes, 2-ethylhexanol, ethylbenzene, mesitylene, mixtures of these compounds or aliphatic hydrocarbons. Preference is given to using 2-ethylhexanol.

The rhodium/diphosphine mixture is then treated with a mixture of carbon monoxide and hydrogen and reacted under a carbon monoxide/hydrogen pressure of 15 to 25 MPa at temperatures of 80 to 150° C. for at least 1 hour to form rhodium complexes which contain the diphosphine as ligands and are insoluble in water and soluble in organic media. Together with the excess of diphosphine dissolved in the organic solvent, they form the catalyst system. The solution of the catalyst composition can then, if the preparation is carried out in a separate apparatus, be transferred into the hydroformylation reactor and admixed with the olefin to be hydroformylated.

If the preparation of the catalyst composition is to be carried out in situ during the hydroformylation reaction, the above-described components, rhodium or rhodium compound and diphosphine, are introduced into the hydroformylation reactor simultaneously with the olefin.

In the formation of the catalyst composition, it has been found to be useful not to use rhodium and the diphosphines of formula I in a stoichiometric ratio, i.e. corresponding to the chemical composition of the rhodium complex which is formed, but to use the diphosphines in excess. The ratio of rhodium and diphosphine can be varied within wide limits and from about 1 to 100 moles of diphosphine can be employed per mole of rhodium. Preference is given to a ratio of rhodium to diphosphine of 1:(1–45). Particular preference is given to using a ratio of 1:(1–25), most preferably a ratio of 1:(1–10).

Rhodium is used either as metal or as a compound. In metallic form, it is used in the form of finely divided particles or deposited in a thin layer on a support such as activated carbon, calcium carbonate, aluminum silicate or alumina. Possible rhodium compounds are those substances which are soluble or suspendable in organic solvents or become soluble or suspendable therein under the reaction conditions.

Suitable compounds are the various rhodium oxides, salts of inorganic hydrogen or oxygen acids, and also salts of aliphatic monocarboxylic or polycarboxylic acids. Examples of rhodium salts are rhodium nitrate, rhodium sulfate, rhodium acetate, rhodium 2-ethylhexanoate, rhodium malonate. In contrast, rhodium-halogen compounds are less suitable because of the low activity of the resulting complexes and because of the corrosive behavior of the halide ions. Furthermore, it is possible to use rhodium carbonyl compounds such as $Rh_3(CO)_{12}$ or $Rh_6(CO)_{16}$ or complex salts of rhodium, e.g. cyclooctadienylrhodium compounds. Preference is given to rhodium oxide, more preferably rhodium acetate and rhodium 2-ethylhexanoate.

It is not necessary to use the diphosphine ligands of formula I in the catalyst composition as uniform compounds. It is also possible, for example, to use different degrees of sulfonation of the diphosphines and/or sulfonate mixtures with various ammonium cations.

In the process of the invention, olefinically unsaturated compounds of 2 to 20 carbon atoms and one or more double bonds are reacted. Suitable olefinically unsaturated compounds are substituted or unsubstituted alkenes of 2 to 20 carbon atoms, substituted or unsubstituted dienes of 4 to 10 carbon atoms, substituted or unsubstituted cycloalkenes or dicycloalkenes of 5 to 12 carbon atoms in the ring system, esters of an unsaturated carboxylic acid having 3 to 20 carbon atoms and an aliphatic alcohol having 1 to 18 carbon atoms, esters of a saturated carboxylic acid of 2 to 20 carbon atoms and an unsaturated alcohol of 2 to 18 carbon atoms, unsaturated alcohols or ethers of 3 to 20 carbon atoms or araliphatic olefins of 8 to 20 carbon atoms The substituted or unsubstituted alkenes of 2 to 20 carbon atoms can be straight-chain or branched alkenes having the double bond in a terminal or internal position. Preference is given to straight-chain olefins of 6 to 18 carbon atoms such as n-hex-1-ene, n-hept-1-ene, n-oct-1-ene, n-non-1-ene, n-dec-1-ene, n-undec-1-ene, n-dodec-1-ene, n-octadec-1-ene and acyclic terpenes. Also suitable are branched alkenes such as diisobutylene (2,4,4-trimethylpent-1-ene), tripropylene, tetrapropylene and dimersol (dibutylene).

Preferred examples of unsubstituted dienes of 4 to 10 carbon atoms are 1,3-butadiene, 1,5-hexadiene and 1,9-decadiene.

Examples of substituted and unsubstituted cycloalkenes or dicycloalkenes of 5 to 12 carbon atoms in the ring system are cyclohexene, cyclooctene, cyclooctadiene, dicyclopentadiene and cyclic terpenes such as limonene, pinene, camphorene and bisabolene.

An example of an araliphatic olef in of 8 to 20 carbon atoms is styrene.

Examples of esters of an unsaturated carboxylic acid of 3 to 20 carbon atoms and an aliphatic alcohol of 1 to 18 carbon atoms are acrylic esters and methacrylic esters with 1 to 18 carbon atoms in the alcohol component.

Example of esters of a saturated carboxylic acid of 2 to 20 carbon atoms and an unsaturated alcohol of 2 to 18 carbon atoms include vinyl and allyl esters having 2 to 20 carbon atoms in the carboxylic acid component.

The unsaturated alcohols and ethers include, for example, allyl alcohols and vinyl ethers.

Based on the olefinically unsaturated compound, use is made of from 5 to 500 ppm by weight, preferably from 10 to 100 ppm by weight and most preferably from 15 to 50 ppm by weight, of rhodium.

The reaction of the olefin with carbon monoxide and hydrogen is carried out at a temperature of from 80 to 150° C., preferably 5 from 100 to 140° C. and particularly from 120 to 130° C., and under a pressure of from 1.5 to 30.0 MPa, preferably from 2.0 to 27.0 MPa and more preferably from 15.0 to 25.0 MPa. The composition of the synthesis gas, i.e. the volume ratio of carbon monoxide and hydrogen, can extend over a wide range and be varied, for example, between 1:10 and 10:1. Use is generally made of gas mixtures in which the volume ratio of carbon monoxide and hydrogen is about 1:1 or deviates only a little from this value.

If desired, the process is carried out in the presence of an organic solvent which is inert under the conditions of the hydroformylation. Suitable solvents are aromatic hydrocarbons such as toluene, ortho-xylene, meta-xylene, para-xylene, mixtures of isomeric xylenes, ethylbenzene, mesitylene, mixtures of these compounds or aliphatic hydrocarbons. However, the hydroformylation reaction can also be carried out without the addition of an organic solvent and, in this case, the olefinic starting compound and the hydroformylation product formed act as solvent.

The reaction of the reactants present in liquid and gaseous phase is carried out in conventional reactors and can be carried out either continuously or batchwise. After the hydroformylation is complete, the reaction product is cooled and freed of gaseous constituents by depressurization. The reaction mixture obtained is then separated off by distillation, extraction or membrane filtration.

The separation of the hydroformylation product from the catalyst composition by distillation, e.g. under reduced pressure, is preferably carried out when the hydroformylation products are thermally stable and do not have very high boiling points.

Removal of the catalyst by extraction is useful when the catalyst can easily be converted into a water-soluble form and then separated off as an aqueous phase by extraction. This process variant enables a gentle separation of the catalyst from the reaction mixture to be achieved. From the aqueous phase, the catalyst can be again converted, possibly by double decomposition, into a water-insoluble form suitable for reuse.

In a particularly suitable embodiment, the hydroformylation products are separated from the catalyst composition by membrane filtration using a semipermeable membrane, preferably using a polyamide membrane, more preferably a polyaramid membrane. Here, the reaction mixture from the hydroformylation, preferably under a pressure of from 1 to 5 MPa, is passed over the membrane to obtain a permeate largely free of the catalyst system, while the catalyst composition comprising rhodium complex and diphosphine ligand accumulates in the retentate.

The retentates containing the catalyst composition can be combined and, if desired, after a further preformation and if desired, after being supplemented with fresh catalyst, be reused in the hydroformylation process. Multiple reuse is possible without appreciable impairment of activity and selectivity of the catalyst composition. A preformation (additional treatment with carbon monoxide and hydrogen) and addition of fresh catalyst (rhodium and/or compound of formula I) can usually be omitted. Handling of the catalyst composition in the active state generally has to be carried out with exclusion of air, since even very small amounts of oxygen damage the catalyst, i.e. deactivate it irreversibly. This is primarily due to the oxidation of P(III) to P(V) in the compound of formula I.

Use of the diphosphines of formula I makes available catalyst compositions which give excellent results when used in the hydroformylation of olefinically unsaturated compounds in a homogeneous phase. In the catalyst composition of the invention, there is no need for a large excess of free, uncomplexed ligand to stabilize the rhodium-diphosphine complexes present, in comparison with previously known homogeneous rhodium-phosphine complexes. This is reflected in a decreased P:Rh ratio.

While according to the prior art, a P/Rh ratio of about 100:1 has to be employed to stabilize the active rhodium-phosphine complexes, the use of the diphosphine ligands of formula I allows a significant reduction in the amount of excess ligand, preferably to a P/Rh ratio of (2–25):1. In addition, rhodium catalyst compositions containing diphosphine ligands of formula I are more active in the hydroformylation in a homogeneous phase under the reaction conditions indicated than are catalyst compositions having a monodentate ligand based on sulfonated triphenylphosphine (TPPTS) having alkylammonium or arylammonium counter ions. This makes it possible to employ a lower rhodium concentration when using the rhodium-diphosphine catalyst compositions.

The above-mentioned advantages are also important in that they particularly favor a separation of the rhodium-diphosphine catalyst composition from the hydroformylation product by membrane filtration during the work-up. As a result of the lower P/Rh ratio, the salt concentration in the hydroformylation mixture is very much lower than in the case of corresponding hydroformylation mixtures which are obtained using rhodium-phosphine catalyst compositions of the prior art. This leads to improved transmembrane flux in carrying out the membrane filtration and therefore significantly smaller membrane areas are required.

In addition, it is possible to concentrate the retentate to a higher level. If this more concentrated retentate containing the catalyst composition is returned to the hydroformylation reactor, a greater proportion of the reactor volume can be utilized for feeding in the reactants. Due to the high molecular weight of the diphosphine compounds of formula I, the retention rates in the membrane filtration are excellent, both for the free diphosphine ligands and also for the rhodium-diphosphine complex.

In the following examples, there are described several preferred embodiments to illustrate the invention. However, it should be understood that the invention is not intended to be limited to the specific embodiments.

EXAMPLE 1

Hydroformylation of propylene using a rhodium/distearylammonium 1,3-bis(di-m-sulfonatophenylphosphino)propane catalyst composition.

a) Preparation of the distearylammonium salt of 1,3-bis(di-m-sulfonatophenylphosphino) propane.

1,3-Bis(diphenylphosphino) propane was sulfonated using oleum and the resulting mixture was hydrolyzed by addition of cold water. The P(III) concentration of the hydrolysis mixture was 42 mmol/kg and 460.6 g of the hydrolysis mixture were placed in a stirred flask. Then, a solution of 96.6 g of distearylamine in 386 g of toluene was added thereto and the mixture was stirred for 60 minutes at 50° C. After completion of stirring, the aqueous phase containing sulfuric acid was separated off and a pH of 2.6 was obtained by addition of 5% strength aqueous sodium hydroxide solution to the organic phase at 45° C. The mixture was allowed to react further for 20 minutes and then 129 g of toluene were added to improve phase separation. After 30 minutes, 662.9 g of an organic phase of the distearylammonium salt of 1,3-bis(di-m-sulfonatophenylphosphino) propane were separated off.

b) Hydroformylation

A 5 liter stirred autoclave was flushed with nitrogen and 500 g of oxygen-free toluene were placed in a glass reservoir provided with nitrogen blanketing. A solution of 103.6 g of the ligand solution from a) and 0.16 mmol of rhodium in the form of a 2-ethylhexanoate salt (15 ppm of Rh; P/Rh ratio: 5) was added and the solution was transferred under nitrogen to the autoclave. A pressure of 27 MPa was then set while stirring by feeding in synthesis gas. After reaching a reaction temperature of 125° C., preformation was allowed to proceed for two hours. 1,300 g of propylene were then pumped from a pressure reservoir into the autoclave over a period of 1 hour and the temperature of 125° C. was maintained by cooling using an air blower. After completion of the propylene feed, the mixture was allowed to react further for 1 hour. The autoclave was then cooled to room temperature and depressurized over a period of 1.5 hours. The contents of the autoclave were transferred with the residual pressure into a 6 liter three-neck flask fitted with an immersed tube and weighed. From the weight increase, a propylene conversion of 93.9% was calculated which corresponded, taking account of the off-gas losses, to virtually complete conversion. Part of the product was taken off and analyzed and a rhodium concentration of 7.96 ppm was measured. The results of the hydroformylation are presented in Table 1.

c) Membrane Filtration 2,261.5 g of the above reaction product were passed through a laboratory membrane filtration unit and the membrane used was polyaramid membrane from Hoechst AG (UF-PA 5 (PET 100)). The membrane was first heated at 100° C. for 15 minutes in water and the reaction product was then passed over the membrane at 150 l/h by a circulation pump and a pressure of 1.5 MPa was set. 91.9% of the product passed through the membrane as permeate and 124.8 g remained as retentate. The transmembrane flux dropped from an initial 92.9 to 59.2 $l/m^2h$ in the final (equilibrium) state as a result of the increase in concentration.

The permeate was membrane-filtered again in a second stage and 93.1% of it passed through the membrane as permeate. The amount of retentate was 144.2 g and the transmembrane flux was initially 119 $l/m^2h$, and in the final (equilibrium) state 75.1 $l/m^2h$. The content of catalyst constituents in the permeate was determined from which a retention value of 96.4% for rhodium was derived, based on the reaction product used.

To demonstrate the recyclability of the membrane-filtered catalyst, the retentates were combined and again used, as described above, in the hydroformylation. The results are shown in Table 2 below. The high transmembrane flux particularly in the final (equilibrium) state, the good retention values and the low absolute catalyst concentration make use of the catalyst system on an industrial scale interesting.

Comparative Examples 1a and 1b

Hydroformylation of propylene using a rhodium/distearylammonium triphenylphosphinetrisulfonate (DSA/TPPTS) catalyst composition.

a) Preparation of the distearylammonium salt of TPPTS 253 g of a Na TPPTs solution were placed in a stirred flask and heated to 65° C. and a solution of 250.3 g of distearylamine in 595 g of toluene was then added. 90 ml of 20% strength sulfuric acid were added while stirring over a period of 60 minutes, until a pH of 2.6 was reached, and the mixture was allowed to react further for 2.5 hours. 170 g of isopropanol were added to improve phase separation and after 15 minutes, 1,037.5 g of an organic phase containing the distearylammonium salt of TPPTS were separated off.

b) Hydroformylation

Comparative Example 1a

The hydroformylation was carried out under the same reaction conditions as described in Example 1 under point b, with the DSA/TPPTS salt being used as ligand. The results are presented in Table 1.

Comparative Example 1b

A 5 liter stirred autoclave was flushed with nitrogen. In a glass reservoir provided with nitrogen blanketing, 845 g of the ligand solution from a) plus 1.17 mmol of rhodium in the form of a 2-ethylhexanoate salt were dissolved (80 ppm of Rh; P/Rh ratio: 100) and transferred under nitrogen into the autoclave. A pressure of 27 MPa was then set while stirring by feeding in synthesis gas. After reaching a reaction temperature of 125° C., the catalyst was left to undergo preformation for two hours. 1,300 g of propylene were then pumped from a pressure reservoir into the autoclave over a period of 1.5 hours and the temperature of 125° C. was maintained by cooling using an air blower. After completion of the propylene feed, the mixture was allowed to react further for 1 hour. The autoclave was then cooled to room temperature and depressurized over a period of 1.5 hours. The contents of the autoclave were transferred under residual pressure into a 6 liter three-neck flask provided with immersed tubes and weighed. From the weight increase, a propylene conversion of 85% was calculated. The results are presented in Table 1.

c) Membrane Filtration

Comparative Example 1a

As can be seen from Table 1, the hydroformylation gave only unsatisfactory conversion of 54.5%, for which reason, a membrane separation of the catalyst composition was omitted.

Comparative Example 1b

The above reaction product from b) was passed through a laboratory membrane filtration unit and the membrane used was a polyaramid membrane from Hoechst AG (UF-PA 5(PET 100)). The membrane was heated at 100° C. in water for 15 minutes and the reaction product was then passed over the membrane at 150 l/h by a circulation pump at a pressure of 1.5 MPa. 87.3% of the product passed through the membrane as permeate and 324.2 g remained as retentate. The transmembrane flux dropped from an initial 103 to 10 l/m²h in the final state as a result of the increase in concentration.

The permeate was membrane-filtered again in a second stage and 90.8% of it passed through the membrane as permeate. The amount of retentate was 234.9 g. The transmembrane flux was initially 136 l/m²h, in the final (equilibrium) state 51 l/m²h. The content of catalyst constituents in the permeate was determined, from which the retention values given in Table 3 were derived, based on the reaction product used.

To demonstrate the recyclability of the membrane-filtered catalyst, the retentates were combined and again used, as described above, in the hydroformylation. The results are shown in Table 3.

Tables 2 and 3 show that in both the 1st and 2nd stages of the membrane filtration, the initial transmembrane flux decreased significantly more for the rhodium/DSA-TPPTS catalyst system than when the rhodium/DSA-chelate ligand catalyst composition as described in Example 1 was used.

TABLE 1

Hydroformylation of propylene

|  |  | Example 1 | Comparative Example 1a | Comparative Example 1b |
|---|---|---|---|---|
| Ligand |  | DSA-chelate | DSA—TPPTS | DSA—TPPTS |
| [Rh] | ppm | 15 | 15 | 80 |
| P:Rh ratio | [mol/mol] | 5 | 5 | 100 |
| Conversion | % | 93.9 | 54.5 | 85 |

Table 1 shows that with both a low rhodium concentration and a low P:Rh ratio, the catalyst composition of the invention (Example 1) gives an excellent conversion. Under analogous experimental conditions, the catalyst compostion using the DSA-TPPTS ligand gives only an unsatisfactory conversion (Comparative Example 1a). Using this catalyst composition, a higher conversion is possible only by a great increase in the rhodium concentration and the P:Rh ratio (see Comparative Example 1b). However, as shown in Table 3, this has a disadvantageous effect on the transmembrane flux during the subsequent membrane filtration.

TABLE 2

Reuse of the membrane-filtered catalyst (rhodium/DSA-chelate ligand) from Example 1

| No. of recirculations | Amount of Rh mg abs. | Conversion (%) | Retention (%) based on input Rh | Transmembrane flux (l/m²h) | | | |
|---|---|---|---|---|---|---|---|
|  |  |  |  | 1st stage | | 2nd stage | |
|  |  |  |  | initial | equilibrium | initial | equilibrium |
| 0 | 18.36 | 93.9 | 96.4 | 92 | 59 | 119 | 75 |
| 1* | 16.98 | 85.4 | 97.7 | 82 | 54 | 112 | 72 |

*0.4 mmol of ligand solution from Example 1 were added to the permeate from the 1st stage

TABLE 3

Comparative Experiment: Reuse of the membrane-filtered catalyst (Rh/DSA—TPPTS)

| No. of recirculations | Conversion (%) | Retention (%) based on input Rh | Transmembrane flux (l/m²h) | | | |
|---|---|---|---|---|---|---|
|  |  |  | 1st stage | | 2nd stage | |
|  |  |  | initial | equilibrium | initial | equilibrium |
| 0 | 85 | 96.0 | 103 | 10 | 136 | 51 |
| 1 | 90 | 99.2 | 97 | 16 | 115 | 40 |
| 2 | 83 | 99.7 | 92 | 17 | 82 | 29 |
| 3 | 92 | 98.9 | 82 | 15 | 75 | 24 |

Various modifications of the catalyst composition and the process of the invention may be made without departing from the spirit or scope thereof and it is to be understood that the invention is intended to be limited only as defined in the appended claims.

What we claim is:

1. A process for preparing aldehydes comprising reacting olefinically unsaturated compounds with carbon monoxide and hydrogen at a temperature of from 80 to 150° C. and under a pressure of 1.5 to 30 MPa in the presence of 1.5 to 30 MPa in the presence of a water-insoluble catalyst composition based on rhodium complexes containing diphosphine ligands, wherein the diphosphine ligands present are compounds of the formula

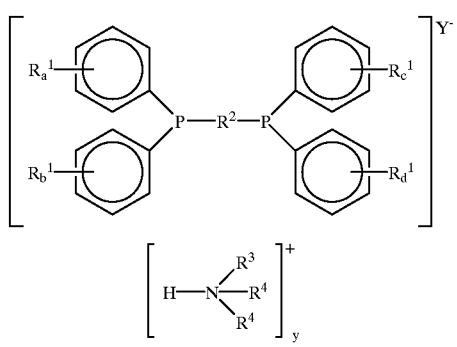

where $R^1$ is selected from the group consisting of carboxylate (COO$^-$), sulfonate (SO$_3^-$), phosphonate (PO$_3^{2-}$) and 2-amino ethanebisphosphonate [NH—CH$_2$—CH(PO$_3^{2-}$)$_2$], $R^2$ is selected from the group consisting of a straight-chain alkylene of 1 to 8 carbon atoms, an oxygen-containing alkylene of 2 to 6 carbon atoms, cycloalkylene of 3 to 10 carbon atoms and a member of the formulae II, III, IV or V

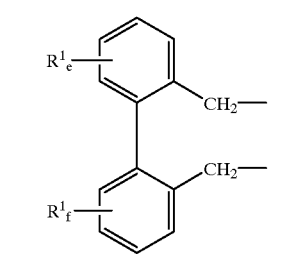

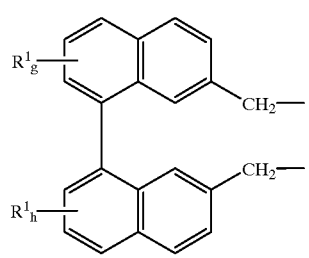

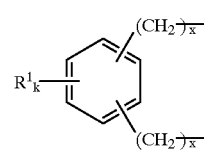

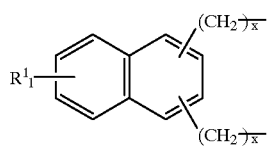

a, b, c, d, e, f, g, h, k and l are individually 0 or 1 where at least one of a, b, c, d, e, f, g, h, k or l has to be equal to 1, x(s) are individually 0 or 1, $R^3$ and $R^4$ are individually selected from the group consisting of alkyl of 4 to 26 carbon atoms, substituted or unsubstituted aryl of 6 to 10 carbon atoms, cycloalkyl of 6 to 10 carbon atoms and benzyl y is an integer of 1 to 24 and $R^3$ can also be hydrogen.

2. The process of claim 1, wherein the catalyst system is prepared in a step upstream of the process or is formed in situ during the process.

3. The process of claim 2, wherein to prepare the catalyst system in an upstream step, the rhodium component and the diphosphine of formula I, each dissolved or suspended in an organic solvent, are combined and reacted under a carbon monoxide/hydrogen pressure of 15 to 25 MPa at a temperature of 80 to 150° for at least 1 hour.

4. The process of claim 1, wherein the olefinically unsaturated compounds used are selected from the group consisting of substituted or unsubstituted alkenes of 2 to 20 carbon atoms, substituted or unsubstituted dienes of 4 to 10 carbon atoms, substituted or unsubstituted cycloalkenes or dicycloalkenes of 5 to 12 carbon atoms in the ring system, esters of an unsaturated carboxylic acid of 3 to 20 carbon atoms and an aliphatic alcohol of 1 to 18 carbon atoms, esters of a saturated carboxylic acid of 2 to 20 carbon atoms and an unsaturated alcohol of 2 to 18 carbon atoms, unsaturated alcohols or ethers of 3 to 20 carbon atoms and araliphatic olefins of 8 to 20 carbon atoms.

5. The process of claim 1, wherein the reaction is carried out in the presence of 5 to 500 ppm by weight of rhodium, based on the olefinically unsaturated compounds.

6. The process of claim 1, wherein the reaction is carried out at a temperature of from 100 to 140° C., and under a pressure of from 2.0 to 27.0 MPa.

7. The process of claim 1, wherein the catalyst system is separated from the reaction mixture after the reaction by distillation, extraction or membrane filtration.

8. The process of claim 7, wherein the membrane filtration is carried out under pressure over a semipermeable membrane.

9. The process of claim 8, wherein the semipermeable membrane used is a polyamide membrane.

10. The process of claim 9, wherein the membrane is a polyaramide membrane.

* * * * *